United States Patent [19]
Golman et al.

[11] Patent Number: 5,985,245
[45] Date of Patent: Nov. 16, 1999

[54] CONTRAST AGENTS FOR MRI USING A MANGANESE COMPOUND AND KOJIC ACID

[75] Inventors: Klaes Golman, Rungsted Kyst, Denmark; Göran Pettersson, Hjärup, Sweden; Arne Berg, Blommenholm, Norway; Jo Klaveness, Oslo, Norway; Pål Rongved, Nesoddtangen, Norway; Peter Leander, Lund, Sweden; Ib Leunbach, Dragör, Denmark

[73] Assignee: Nycomed Imaging AS, Oslo, Norway

[21] Appl. No.: 08/963,198

[22] Filed: Nov. 3, 1997

Related U.S. Application Data

[63] Continuation of application No. 08/462,873, Jun. 5, 1995, abandoned.

[30] Foreign Application Priority Data

Aug. 18, 1994 [GB] United Kingdom .................... 9416767

[51] Int. Cl.[6] .................................................. A61B 5/055
[52] U.S. Cl. ...................... 424/9.36; 424/9.32; 424/9.35; 424/9.3; 424/9.361
[58] Field of Search .................................... 424/9.3, 9.32, 424/9.35, 9.36, 9.361; 436/173; 600/420

[56] References Cited

U.S. PATENT DOCUMENTS

| | | | |
|---|---|---|---|
| 5,128,121 | 7/1992 | Berg et al. .................................. | 424/9 |
| 5,143,716 | 9/1992 | Unger ......................................... | 424/9 |
| 5,292,729 | 3/1994 | Ashmead . | |
| 5,314,681 | 5/1994 | Leunbach et al. .......................... | 424/9 |

FOREIGN PATENT DOCUMENTS

| | | |
|---|---|---|
| 0 401 096 A1 | 5/1990 | European Pat. Off. . |
| 0 524 633 A2 | 7/1992 | European Pat. Off. . |
| WO 87/04622 | 8/1987 | WIPO . |
| WO 93/06811 | 4/1993 | WIPO . |

OTHER PUBLICATIONS

Formulation of Radiographically Detectable Gastrointestinal Contrast Agents for Magnetic Resonance Imaging: Effects of a Barium Sulfate Additive on MR Contrast Agent Effectiveness, Rubin et al., Magnetic Resonance in Medicine 23, 154–165 (1992).

Chromium and Chronic Ascorbic Acid Depletion Effects on Tissue Ascorbate, Manganese, and [14]C Retention from [14]C-Ascorbate in Guinea Pigs, Seaborn et al., Biological Trace Element Research, vol. 41, 1994.

Effects of Copper, Iron, and Ascorbic Acid on Manganese Availability to Rats, P.E. Johnson, et al., P.S.E.B.M, vol. 199, 470–480, 1992.

Efectele Tratamentului Acut Cu Mangan Asupra Unor Parametri Biochimici La Puii De Gaina, R. Giurgea et al., Studii si cercetari de Biologie seria biologie animala, Decembre 1992.

Trace Element Absorption in Infants as a Foundation to Setting Upper Limits for Trace Elements in Infant Formulas[1], Bo Lonnerdal, The Journal of Nutrition, vol. 119, No. 12S, 1988.

Higher Retention of Manganese in Suckling Than in Adult Rats is Not Due to Maturational Differences in Manganese Uptake by Rat Small Intestine, Janet G. Bell et al., Journal of toxicology and Environmental Health, vol. 26, No. 4, 1989.

Stability of Yttrium (III) Complexes of Substituted 3–Hydroxy–4H–Pyran–4–ones in Aqueous Solution, R. Petrola, Finnish Chemical Letters, vol. 13, No. 5, pp. 129–135, 1986.

Thermodynamics of Kojate Complexes of the Lanthanides, R. Stampfli et al., Journal of Coordination Chemistry, vol. 1, No. 3, pp. 173–178, Feb. 1972.

Stabilités thermodynamiques des complexes de l'acide kojique, un a–cétoénol, avec des cations divalents: Mn, Co, Ni, Cu et Zn, C. Gérard et al., Bull. Soc. Chim. Fr., No. 11–12, Pt. 1, pp. 2404–2408, 1975.

Sommaire de la Premiére Partie Chimie Analytique, Minérale et Physicochimie, Bull. Soc. Chim. Fr., No. 11–12, Pt. 1, pp. 451–456, 1979.

*Primary Examiner*—Jose' G. Dees
*Assistant Examiner*—Michael G. Hartley

[57] ABSTRACT

There is provided a contrast medium composition comprising: (a) a first contrast agent comprising a physiologically tolerable manganese compound, a physiologically tolerable reducing compound containing an α-hydroxy ketone group, or salt thereof, having a manganese concentration of at least 0.3 mM or being in a dosage unit form containing at least 300 μmol manganese, together with (b) a second contrast agent. Such compositions have been found to be particularly suited to imaging of the liver.

10 Claims, 13 Drawing Sheets

EFFECT OF DIFFERENT DOSES OF $Mn^{2+}$-CHLORIDE*
ON LIVER ENHANCEMENT

* ALL SOLUTIONS CONTAINED ASCORBIC ACID;
DOSE = 0.1 mmol/kg

ADDITION OF ASC. ACID OR ASC. ACID - PALMITATE
TO Mn-CHLORIDE (0.2 mmol/kg)

ADDITION OF ASCORBIC ACID OR KOIJIC ACID
TO Mn-CHLORIDE (0.2 mmol/kg)

MnCl$_2$
A PHARMACOKINETIC STUDY IN THE RAT

CONTRAST AGENTS FOR MRI USING A MANGANESE COMPOUND AND KOJIC ACID

This application is a continuation of application Ser. No. 08/462,873, filed on Jun. 5, 1995, now abandoned.

The present invention relates to improvements in and relating to magnetic resonance imaging (MRI) and in particular to compositions for use as or in the preparation of MRI contrast media for imaging of the liver, bile duct a gall bladder.

MRI is now well established as a medical diagnostic tool. The ability of the technique to generate High quality images and to differentiate between soft tissues without requiring the patient to be exposed to ionizing radiation has contributed to this success.

Although MRI can be performed without using added contrast media, it has been found that substances which affect the nuclear spin reequilibration of the nuclei (hereinafter the "imaging; nulei"—generally water protons in body fluids and tissues) responsible for the magnetic resonance (MR) signals from which the images are generated may be used to enhance image contrast and, accordingly, in recent years, many such materials have been suggested as MRI contrast agents.

The enhanced contrast obtained with the use of contrast agents enables particular organs or tissues to be visualized more clearly by increasing or by decreasing the signal level of the particular organ or tissue relative to that of its surroundings. Contrast agents raising the signal level of the target site relative to that of its surroundings are termed "positive" contract agents whilst those lowering the signal level relative to surroundings are teamed "negative" contrast agents.

The majority of materials now being proposed as MRI contrast media achieve a contract effect because they contain paramagnetic, superparamagnetic or ferromagnetic species.

For ferromagnetic and superparamagnetic contrast agents, which are negative MRI contrast agents, the enhanced image contrast derives primarily from the reduction in the spin reequilibration parameter know as $T_2$ or as the spin-spin relation time, a reduction arising from the effect on the imaging nuclei of the fields generated by the ferromagnetic or superparamagnetic particles.

Paramagnetic contrast agents on the other hand may be either positive or negative MRI contrast agents. The effect of paramagnetic substances on magnetic resonance signal intensities is dependent on many factors, the most important of which a the concentration of the paramagnetic substance at the imaged site, the nature of the paramagnetic substance itself and the pulse sequence and magnetic field strength used in the imaging routine. Generally, however, paramagnetic contrast agents are positive MRI contrast agents at low concentrations where their $T_1$ lowering effect dominates and negative MRI contrast agents at higher concentrations where heir $T_2$ lowering effect is dominant. In either event, the relaxation time reduction results from the effect on the imaging nuclei of the magnetic fields generated by the paramagnetic centres.

The use of paramagnetic, ferromagnetic and superparamagnetic materials as MRI contrast agents has been widely advocated and broad ranges of suitable materials have been suggested in the literature.

An example of a physiologically tolerable paramagnetic material known for use as an MRI contrast agent is manganese ion, which may conveniently be used in the form of its salts or chelates. Indeed, even at very low i.v. dosages (about 5–10 μmol/kg bodyweight) manganese has been found to be particularly effective as a contrast agent for imaging of the liver.

However manganese, when administered intravenously as a contrast agent, may be teratogenic at clinical dosages. Administered intravenously, manganese is also known to interfere with the normal functioning of the heart by replacement of calcium in the calcium pump of the heart.

In order to reduce the direct effect on the heart, oral administration bas beer proposed. This ensures passage of the contrast agent trough the liver before going to the heart.

Oral administration of $MnCl_2$ as a liver imaging MR contrast agent has been proposed and orally administered MnCl2 has not heen found to be teratogenic. However, the absorption of $MnCl_2$ through the gut is poor, and as a result the dosage required for clinical efficacy is of the order of 200 μmol/kg bodyweight. In the event of damage to the gut resulting in increased uptake, such a high dosage level still has the potential for causing undesired adverse effects, eg. cardiac effects.

We have now surprisingly found that gastrointestinal tract manganese contrast agents suitable for imaging of the liver may be produced by the incorporation of a reducing compound containing an α-hydroxy ketone group (—C (OH)—CO—) as an uptake promoter.

Thus, viewed from one aspect the present invention provides a contrast medium composition comprising a physiologically tolerable manganese compound, a physiologically tolerable reducing compound containing an α-hydroxy ketone group, or salt thereof and a physiologically tolerable carrier or excipient, having a manganese concentration of at least 0.3 mM or being in a dosage unit form containing at least 300 μmol manganese.

The manganese compound, which preferably is soluble in gastrointestinal fluid may for example be a chelate or a salt. Particularly preferred are metal chelates and salts in which the manganese is present as Mn(II) rather than Mn(III) since the former has a higher magnetic moment and thus is more effective as an MR contrast agent.

The reducing nature of the uptake promoter is important since normal uptake or manganese by the gut tends to favour Mn(II) rather than Mn(III).

Preferred compositions according to the invention are those in which the reducing compound further contains an oxygen atom in a heterocyclic ring structure.

Particularly preferred as an uptake promoter in the compositions of the invention in ascorbic acid which has been found to increase the uptake of manganese in the liver by a factor of about 5 compared with oral administration of $MnCl_2$ alone. This surprising increase is demonstrated in the Figures of the accompanying drawings. Moreover ascorbic acid (vitamin C) is particularly preferred as an uptake promoter since it is cheap, readily available and particularly well tolerated by the body.

Yet more particularly preferred compositions in accordance with the invention are those in which the uptake promoter in kojic acid; The dramatic increase in the uptake of manganese In the liver following administration of $MaCl_2$+kojic acid can be seen from FIG. 5 of the accompanying drawings.

Using the compositions of the invention, the liver can be effectively imaged with a significant reduction in the dosage of manganese required. Thus, for example, a 50% enhancement of the liver can be obtained by oral administration of 100 μmol manganese/kg body weight and 1 mmol/kg ascorbic acid. Such a dosage results in the same degree of enhancement of the liver as 5 μmol Mn(II) kg body weight $MnCl_2$ (i.v.) or as 500 μmol Mn(II)/kg body weight $MnCl_2$ (p.o.).

FIG. 1 hereto demonstrates the effect of p.o. administration of MnCl$_2$ and ascorbic acid on liver enhancement compared with p.o. administration of MnCl$_2$ Increase in the ratio of ascorbic acid to MnCl$_2$ results in an increase in the enhancement effect obtained. This dose-response relationship can be seen from FIG. 2 hereto.

The gradual increase in enhancement of the liver with time following administration of a composition in accordance with the invention enables the dynamics of uptake of the contrast agent by the liver to be monitored (see for example FIG. 2). This is of particular importance in enabling identification of areas of healthy tissue and areas of possible tumor growth.

In the compositions according to the invention, the preferred molar ratio of manganese to uptake promoter is from 1:0.2 to 1:50, eg. 1:1 to 1:20, especially 1:3 to 1:6, particular preferably about 1:5.

The uptake promoter may if desired be present in whole or in part as the counterion to the manganese ions. Thus in one embodiment the composition of the invention comprises as both manganese compound and uptake promoter a manganese salt of a reducing compound containing an α-hydroxy ketone group, eg. manganese (II) ascorbate.

The compositions according to the invention may be used to achieve a so-called "double contrast effect" by increasing the signal level from the liver whilst at the same time decreasing that from the surrounding tissues, in particular from the gut. Such an effect enables yet further enhancement of the liver.

A double contrast effect can be achieved with the compositions of the invention since the resulting manganese ion concentration within the g.i. tract will generally be such as to create a signal suppressing effect there. In this case, to avoid image artefacts resulting from pockets of the gut being contrast agent free, it is desirable to incorporate in the compositions a viscosity enhancing agent and desirably also an osmoactive agent. Examples of suitable viscosity enhancers aid osmoactive agents are described in WO 91/01147 and WO 91/01148.

In a particularly preferred embodiment, the compositions of the invention may be used in combination with a second contrast agent laving either a positive or negative contrast effect. Preferably the compositions of the invention are used in combination with a second contrast agent having an opposing contrast effect; This results in a "double contrast effect" enabling visualisation of the liver to be particularly enhanced.

As mentioned above, paramagnetic materials such as manganese ions may act as either positive or negative MRI contrast agents depending upon a number of factors, including the concentration of the ions at the imaging site and the magnetic field strength used in the imaging procedure. At the concentrations of manganese contemplated for use in the compositions of the invention, the manganese-containing contrast agent will, in general, function as a positive contrast agent. The second contrast agent is therefore conveniently a negative contrast agent and my be any negative MRI contrast agent suitable for oral administration. However, as indicated above, any MR contrast agent, negative or positive, may ba used.

Examples of negative MRI contrast agents for use in combination with the compositions of the invention include known ferromagnetic and superparamagnatic species, such as for example magnetic iron oxide particles either free or enclosed within or bound to a non-magnetic matrix material such as a polysaccharide eg. LUMIREM and sulphonated polystyrene eg. ABDOSCAN®.

Further examples of contrast agents for use in combination with the compositions of the invention include Gd and Dy ions bound to a polymeric matrix, for example LUMIREM or GADOLITE (Gadolinium alumina silicate oral suspension).

When, using the compositions of the invention to achieve a double contrast effect, it is particularly preferable to incorporate a viscosity enhancing agent which attains its full viscosity enhancing effect only after administration of the contrast medium. The contrast medium is thus ale to be ingested in a relatively tolerable form while yet developing the desired viscosity at or during passage towards the site which is to be imaged.

The compositions of the invention are particularly suited to use, if required after dispersion in aqueous media, for imaging of the liver. For such a purpose the compositions may be administered into the gastrointestinal tract orally, rectally or via a stomach tube.

Thus, viewed from a further aspect the preset invention provides a method of generating a magnetic resonance image of a human or non-human, preferably mammalian, animal body which, method comprises administering into the gastrointestinal tract of a said body a contrast medium comprising a physiologically tolerable manganese compound and a physiologically tolerable reducing compound containing an α-hydroxy ketone group or salt thereof and generating a magnetic resonance image of the liver and abdomen of said body.

Viewed from a yet further aspect the invention also provides a method of generating a magnetic resonance image of a human or non-human animal boy, which method comprises administering into the gastrointestinal tract of a said body an effective amount of a composition comprising: (a) a first contract agent comprising a physiologically tolerable manganese compound, a physiologically tolerable reducing compound containing an α-hydroxy ketone group, or salt thereof, having a manganese concentration of at least 0.3 mM or being in a dosage unit form containing at least 300 μmol manganese, together with (b) a second contrast agent and generating a magnetic resonance image of the liver and abdomen of said body.

It in possible to formulate the contrast medium immediately or shortly prior to administration by mixing the reducing compound with the manganese species. Thus, in a further aspect the invention also provides an MRI contrast agent kit comprising in a first container a physiologically tolerable manganese compound, and in a second container a physiologically tolerable reducing compound containing an α-hydroxy ketone group, or salt thereof.

Viewed from a further aspect the invention also provides an MRI contrast agent kit comprising in a first container a first contrast agent comprising a physiologically tolerable manganese compound, a physiologically tolerable reducing compound containing an α-hydroxy ketone group, or salt thereof, having a manganese concentration of at least 0.3 mM or being in a dosage unit form containing at least 300 μmol manganese, and in a second container a second contrast agent comprising a particulate ferromagnetic or superparamagnetic material or Gd or Dy ions bound to a polymeric matrix.

The contrast agent compositions of the invention may of course include components other than the uptake promoter, the manganese compound, the viscosity enhancing and osmoactive agents, for example conventional pharmaceutical formulation aids such as wetting agents, buffers, disintegrants, binders, fillers, flavouring agents and liquid carrier media such as sterile water, water/ethanol etc.

For oral administration, the pH of the composition is preferably in the acid range, eg. 3 to 8 and while the reducing compound may itself serve to yield a composition with this pH, buffers or pH adjusting agents may be used.

The contrast media may be formulated in conventional pharmaceutical administration forms, such as tablets, capsules, powders, solutions, dispersions, syrups, suppositories etc.

The preferred dosage of the composition according to the present invention will vary according to a number of factors, such as the administration route, the age, weight and species or the subject and the particular uptake promoter used. Conveniently, the dosage of manganese will be in the range of from 5 to 150 $\mu$mol/kg bodyweight, preferably from 10 to 100 $\mu$mol/kg bodyweight, while the dosage of the uptake promoter will be in the range of from 5 $\mu$mol to 1 mmol/kg bodyweight, preferably from 25 $\mu$mol to 0.5 mmol/kg bodyweight.

Preferred embodiments of the invention will now be described by reference to the following non-limiting Examples and the accompanying drawings, in which.

Figure 1:
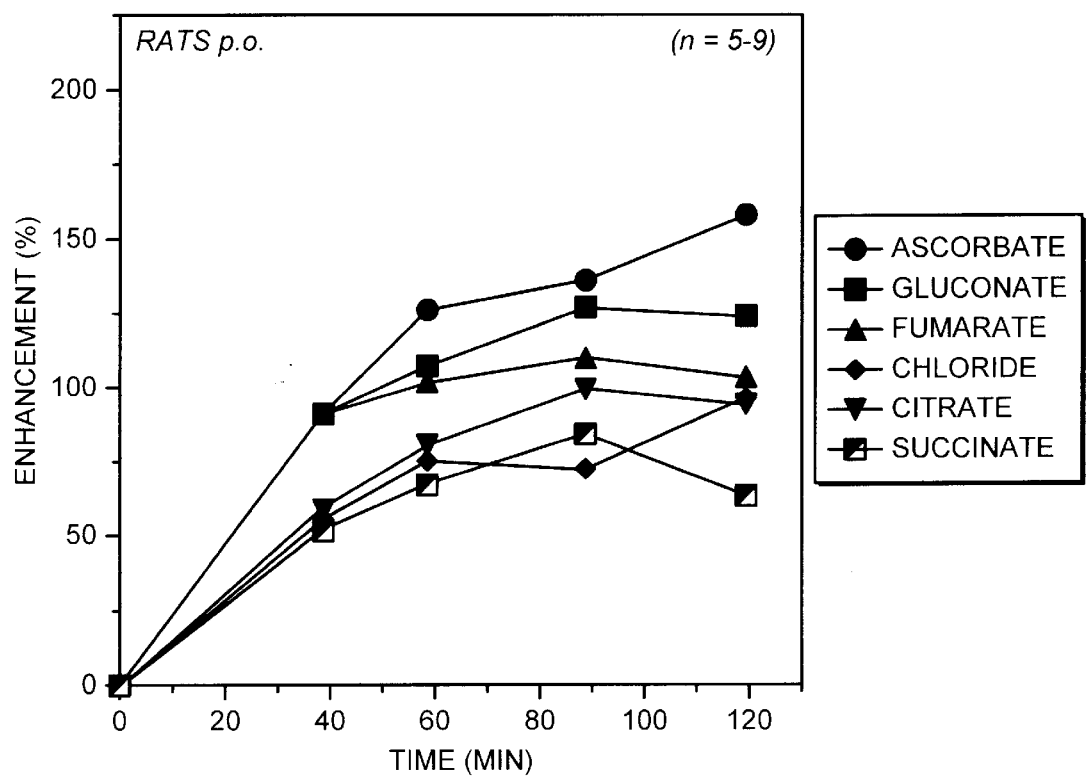
FIG. 1 is a graph illustrating the effect of p.o. administration of different $Mn^{2+}$ salts on liver enhancement.

For the measurement of the curves of FIGS. 1 to 7 the following materials were used:

FIG. 1
Mn-ascorbate

| | | |
|---|---|---|
| $MnCl_2 \times 2H_2O$ | | 6.48 g |
| Ascorbic acid | | 35.2 g |
| Water | ad | 1000 ml |

Mn-gluconate

| | | |
|---|---|---|
| Mn-gluconate | | 19.2 g |
| Water | ad | 1000 ml |

Mn-citrate

| | | |
|---|---|---|
| $MnCl_2 \times 2H_2O$ | | 6.48 g |
| $Na_3$-citrate $\times 2H_2O$ | | 23.5 g |
| Water | ad | 1000 ml |

Figure 2:
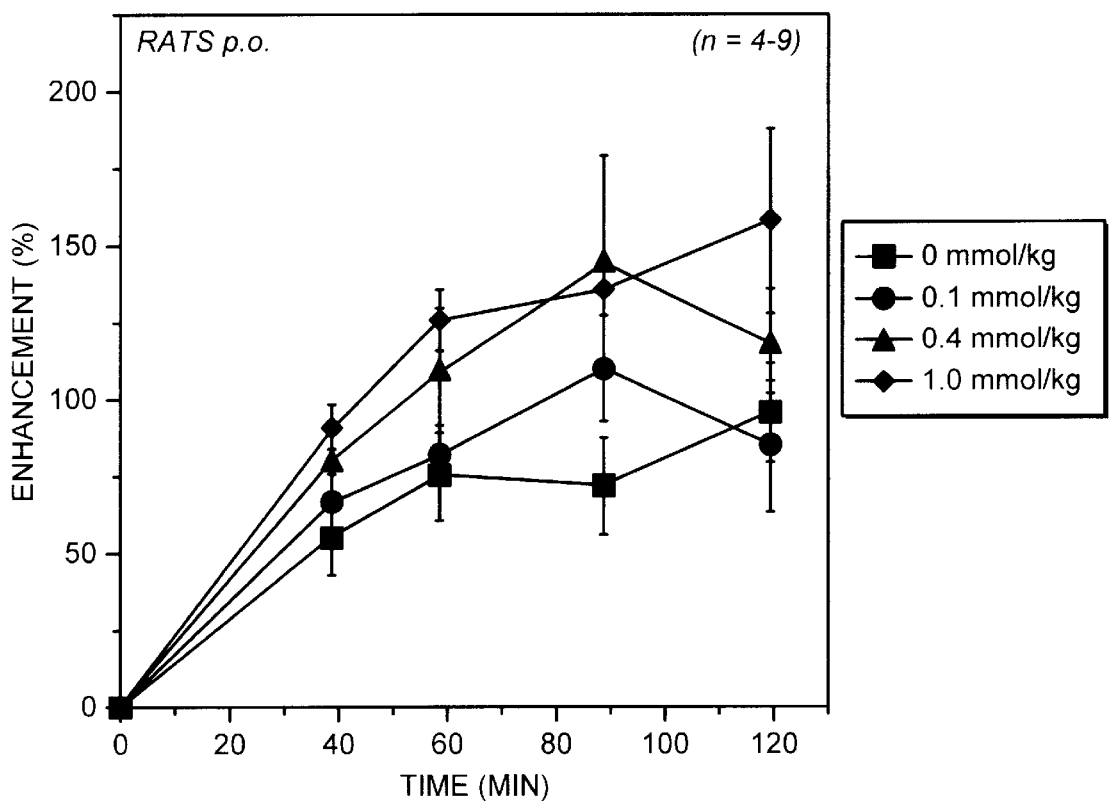
FIG. 2 is a graph illustrating the effect of p.o. administration of $MnCl_2$+ascorbic acid on liver enhancement at varying concentrations of ascorbic acid.

FIG. 2
$MnCl_2$

| | | |
|---|---|---|
| $MnCl_2 \times 2H_2O$ | | 6.48 g |
| Water | ad | 1000 ml |

$MnCl_2$ + 0.1 mmol/kg ascorbic acid

| | | |
|---|---|---|
| $MnCl_2 \times 2H_2O$ | | 6.48 g |
| Ascorbic acid | | 3.52 g |
| Water | ad | 1000 ml |

$MnCl_2$ + 0.4 mmol/kg ascorbic acid

| | | |
|---|---|---|
| $MnCl_2 \times 2H_2O$ | | 6.48 g |
| Ascorbic acid | | 14.1 g |
| Water | ad | 1000 ml |

$MnCl_2$ + 1.0 mmol/kg ascorbic acid

| | | |
|---|---|---|
| $MnCl_2 \times 2H_2O$ | | 6.48 g |
| Ascorbic acid | | 35.2 g |
| Water | ad | 1000 ml |

Figure 3:
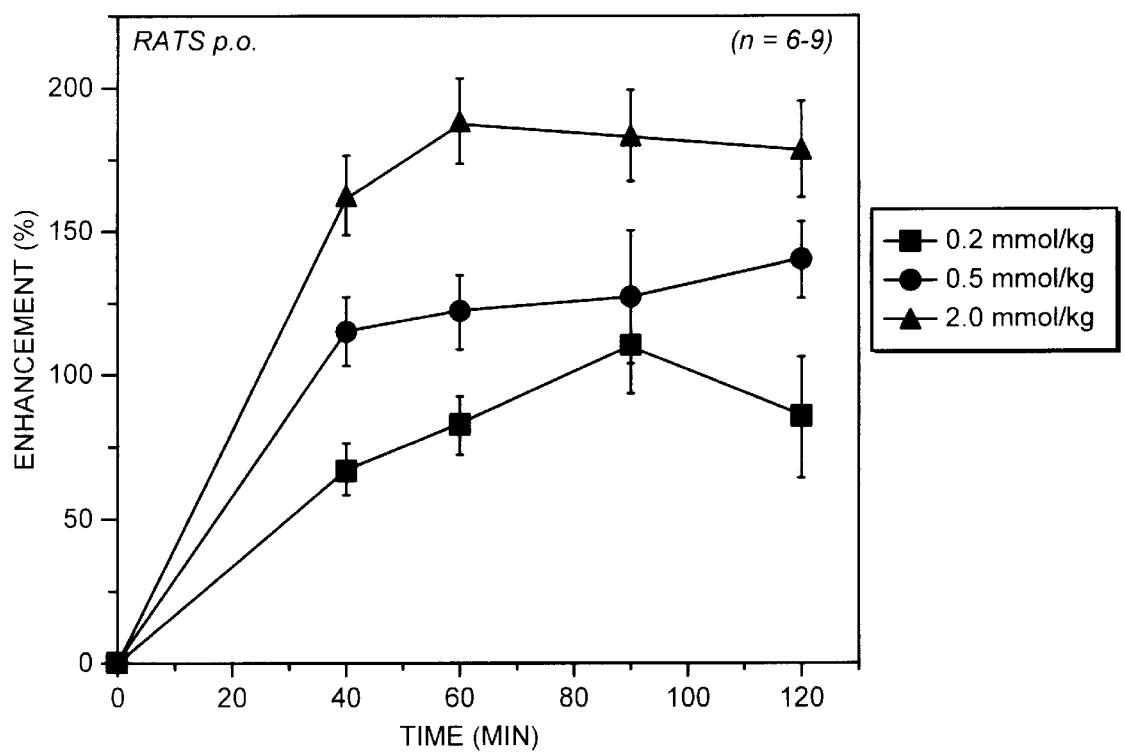
FIG. 3 is a graph illustrating the effect of p.o. administration of different doses of $MnCl_2$ containing 0.1 mmol/kg ascorbic acid on liver enhancement.

FIG. 3
$MnCl_2$ (0.2 mmol/kg) + ascorbic acid

| | | |
|---|---|---|
| $MnCl_2 \times 2H_2O$ | | 6.48 g |
| Ascorbic acid | | 3.52 g |
| Water | ad | 1000 ml |

$MnCl_2$ (0.5 mmol/kg) + ascorbic acid

| | | |
|---|---|---|
| $MnCl_2 \times 2H_2O$ | | 16.2 g |
| Ascorbic acid | | 3.52 g |
| Water | ad | 1000 ml |

$MnCl_2$ (2.0 mmol/kg) + ascorbic acid

| | | |
|---|---|---|
| $MnCl_2 \times 2H_2O$ | | 64.8 g |
| Ascorbic acid | | 3.52 g |
| Water | ad | 1000 ml |

Figure 4:
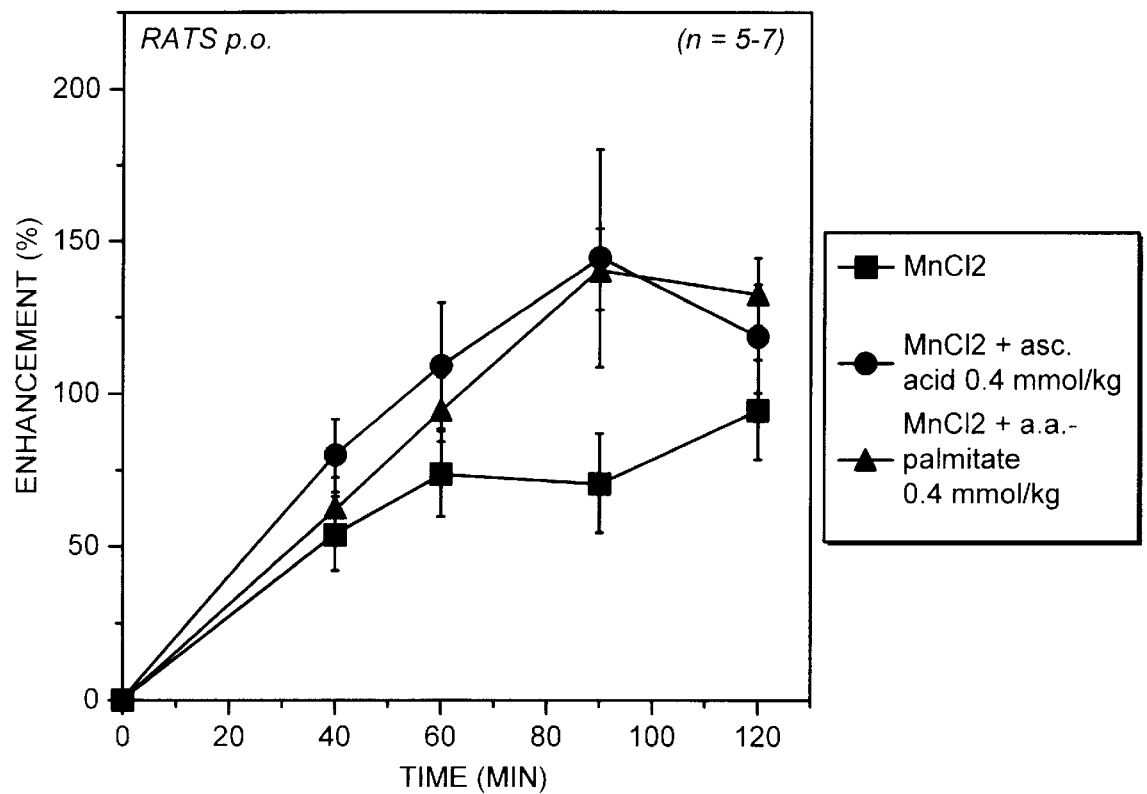
FIG. 4 is a graph illustrating the effect of the addition of ascorbic acid or ascorbic acid-palmitate to $MnCl_2$ on enhancement of the liver.

FIG. 4
$MnCl_2$

| | | |
|---|---|---|
| $MnCl_2 \times 2H_2O$ | | 13.0 g |
| Water | ad | 1000 ml |

$MnCl_2$ + ascorbic acid - palmitate (0.4 mmol/kg)

| | | |
|---|---|---|
| L-ascorbic acid 6-palmitate | | 66.4 g |
| Polyethylene glycol 300 | ad | 1000 ml |

Figure 5:
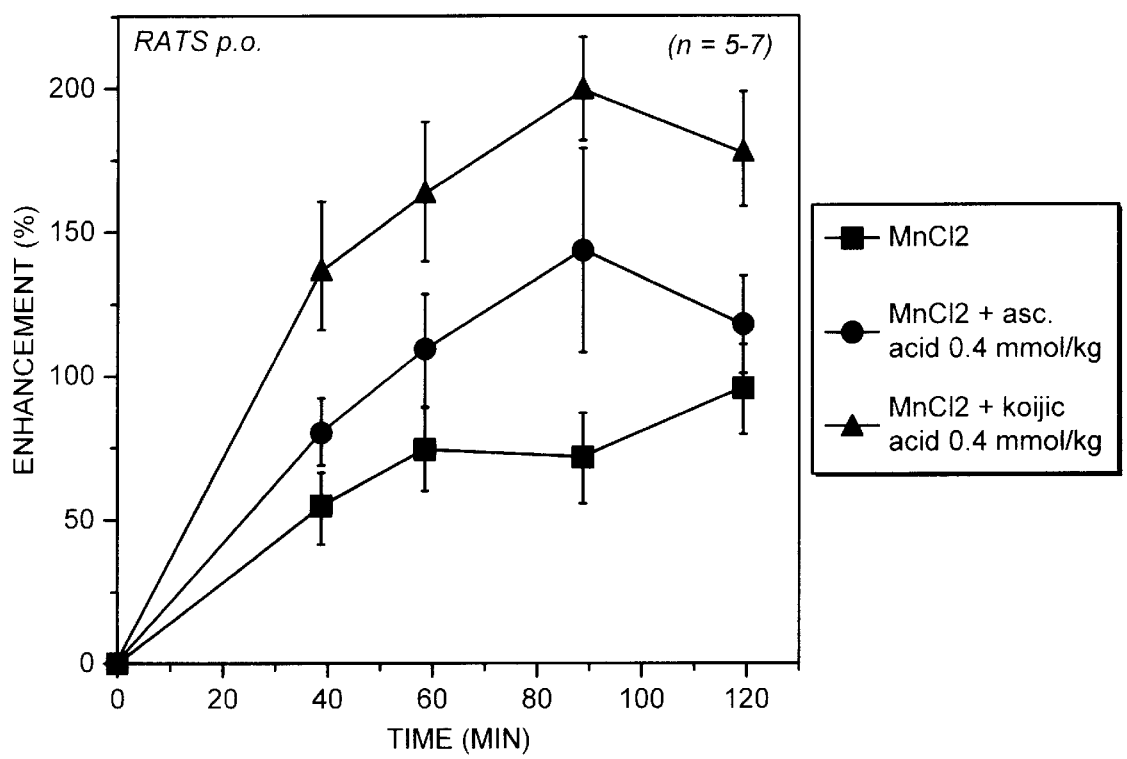
FIG. 5 is a graph illustrating the effect of the addition of ascorbic acid or kojic acid to $MnCl_2$ on enhancement of the liver.
Figure 6:
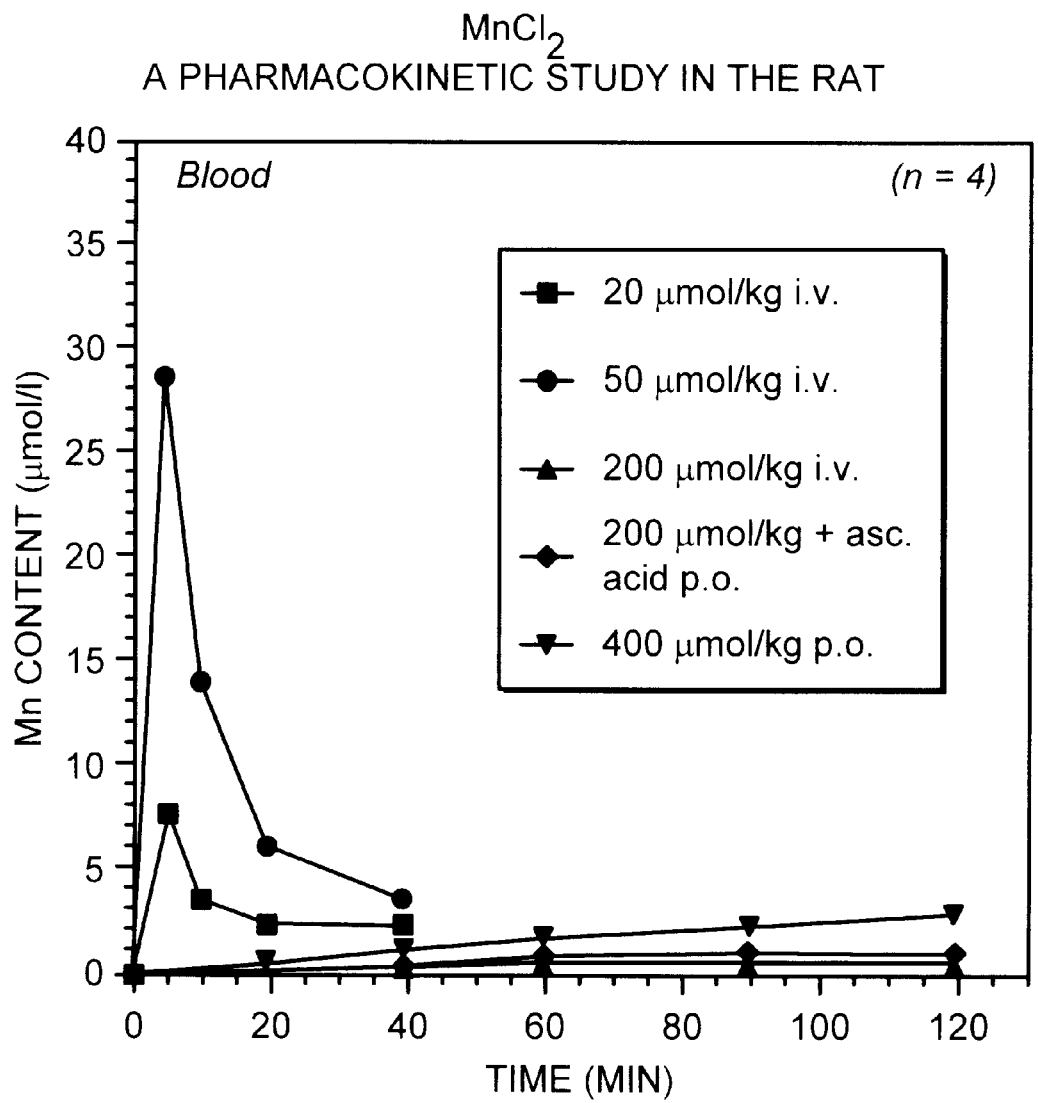
FIG. 6 is a graph illustrating the results of a pharmacokinetic study to determine the variation in concentration of Mn(II) in the blood following administration of various Mn(II)-containing compositions.
Figure 7:
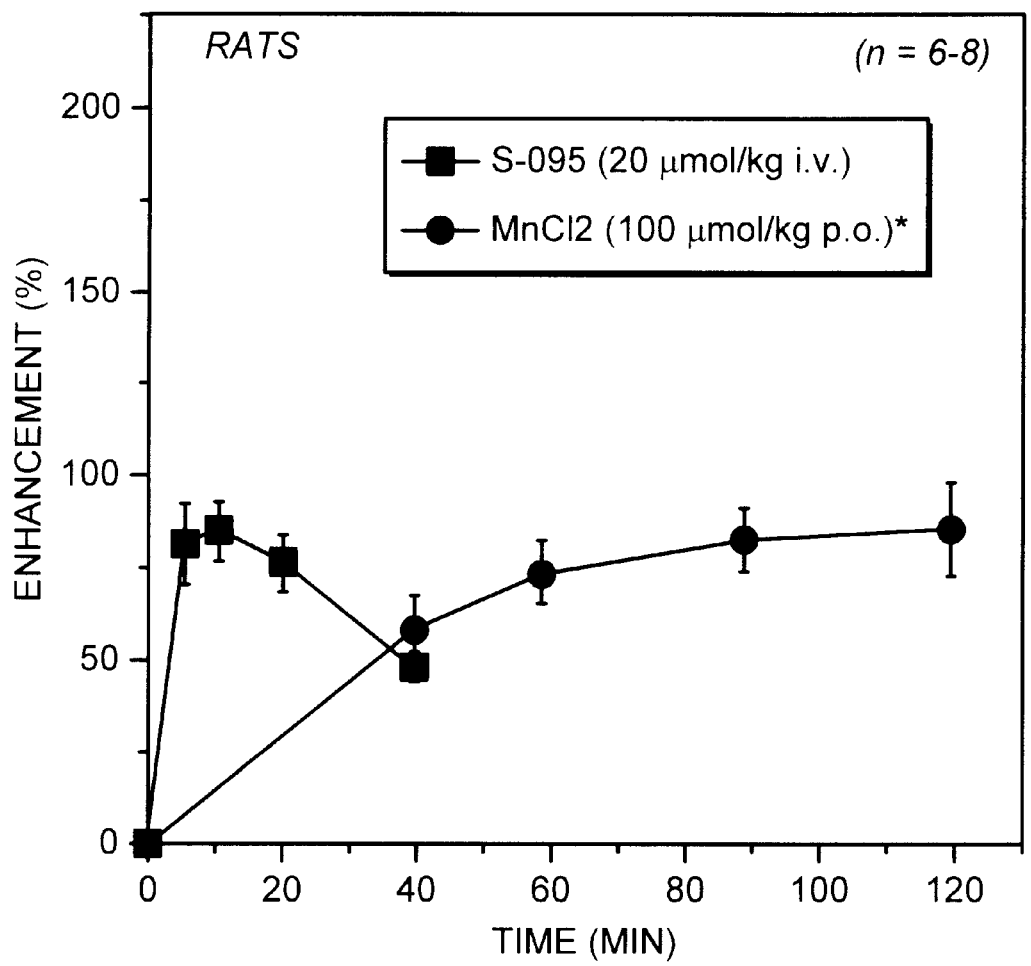
FIG. 7 is a graph comparing the effect on liver enhancement of i.v. administration of Mn DPDP (S-095) with that of p.o. administration of $MnCl_2$+ascorbic acid.
Figure 8:
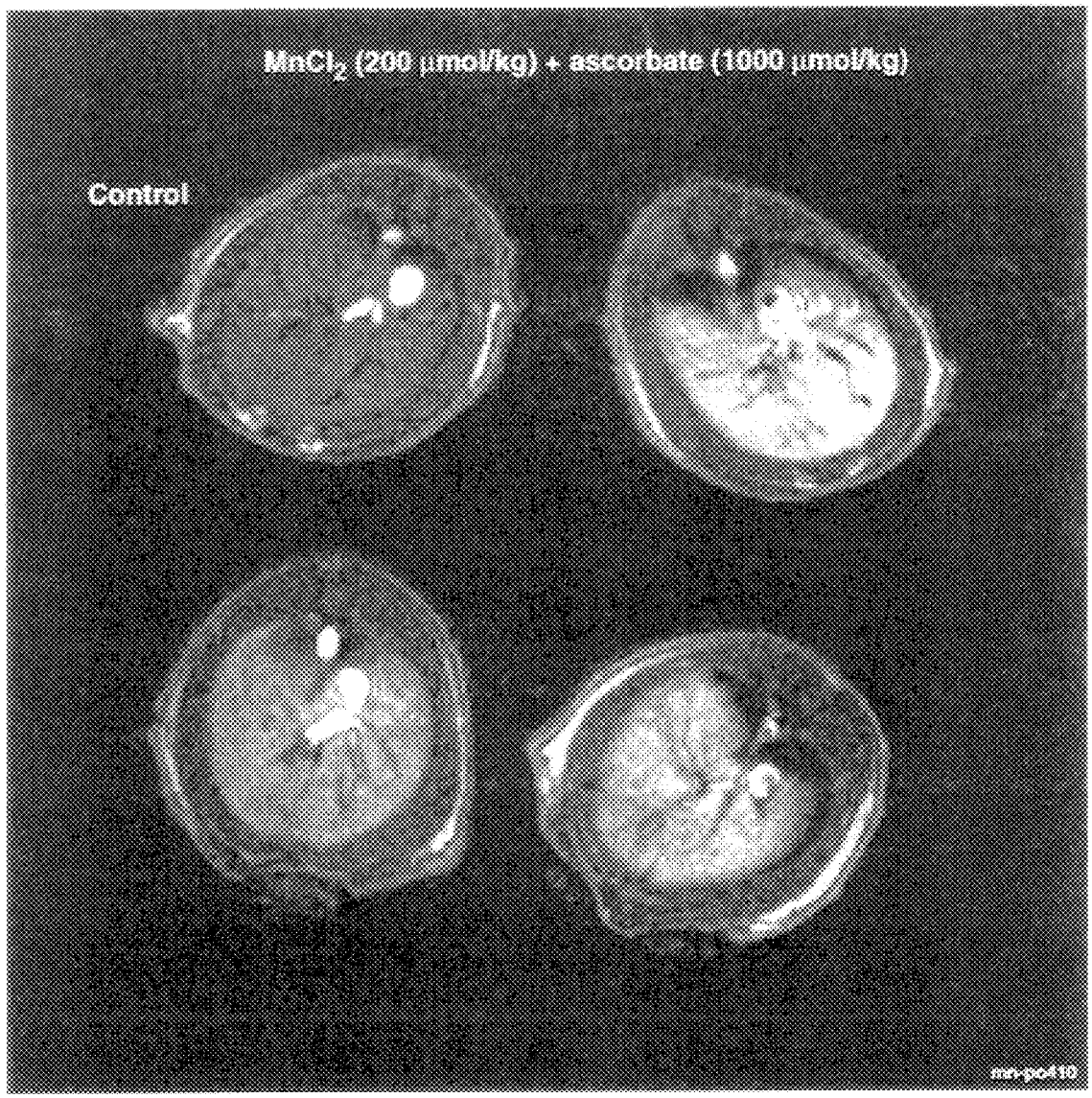
FIG. 8 illustrates transversal T1-weighted (SE 57/13; 2.4 T) liver images from a control rat and from three rats 2 hours after oral administration of 200 $\mu$mol/kg $MnCl_2$+1000 $\mu$mol/kg ascorbate. The signal intensity of the liver is substantially increased after gavage administration of $Mn^{2+}$ and ascorbate.
Figure 9:
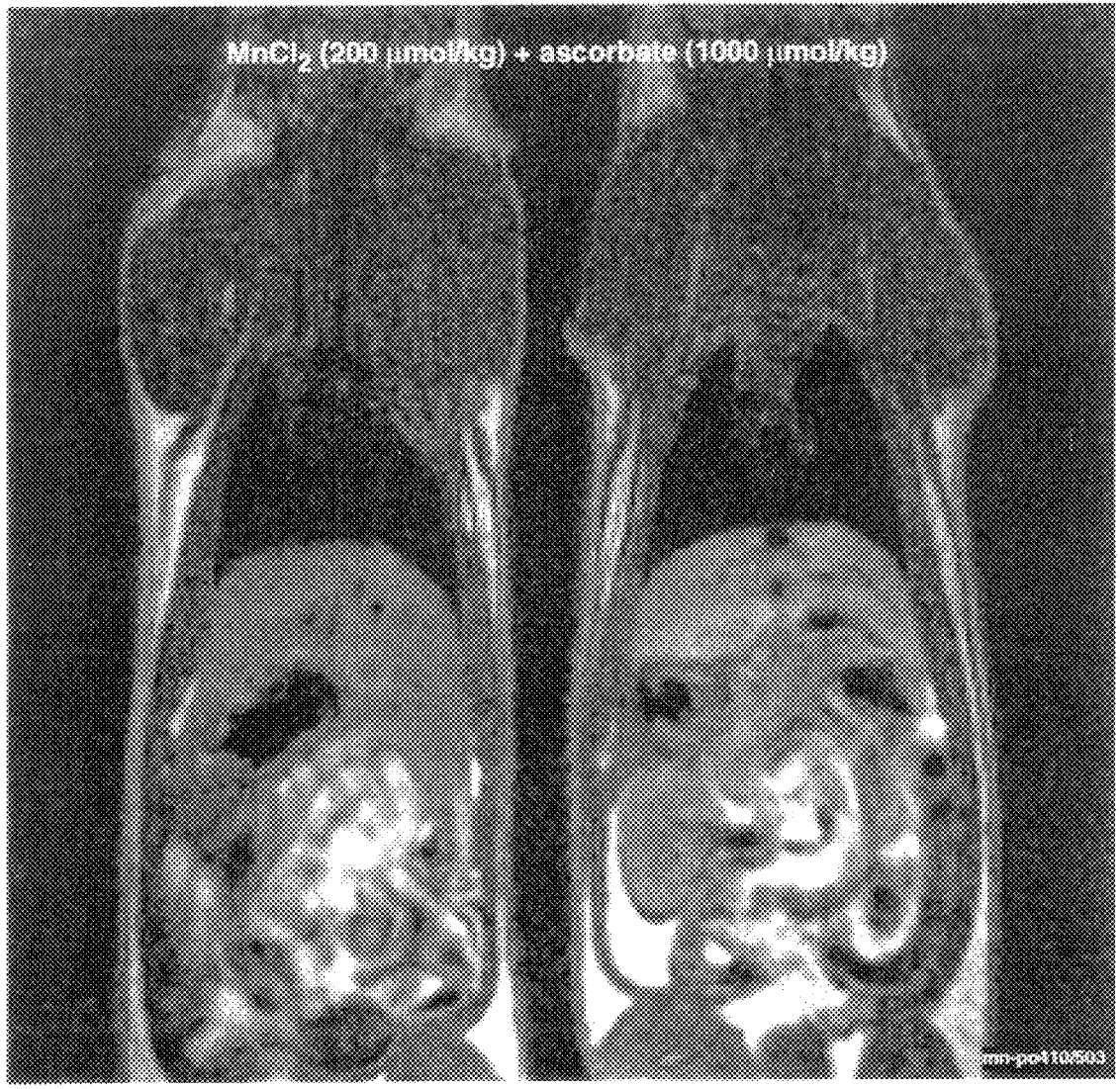
FIG. 9 illustrates coronal T1-weighted (SE 90/17; 2.4 T) liver image from two rats 2 hours after oral administration of 200 $\mu$mol/kg $MnCl_2$+1000 $\mu$mol/kg ascorbate. The signal intensity in the gastrointestinal lumen is reduced after administration of $Mn^{2+}$.

FIG. 5
$MnCl_2$ + kojic acid (0.4 mmol/kg)

| | | |
|---|---|---|
| $MnCl_2 \times 2H_2O$ | | 6.48 g |
| Kojic acid | | 11.4 g |
| Water | ad | 1000 ml |

Figure 10:
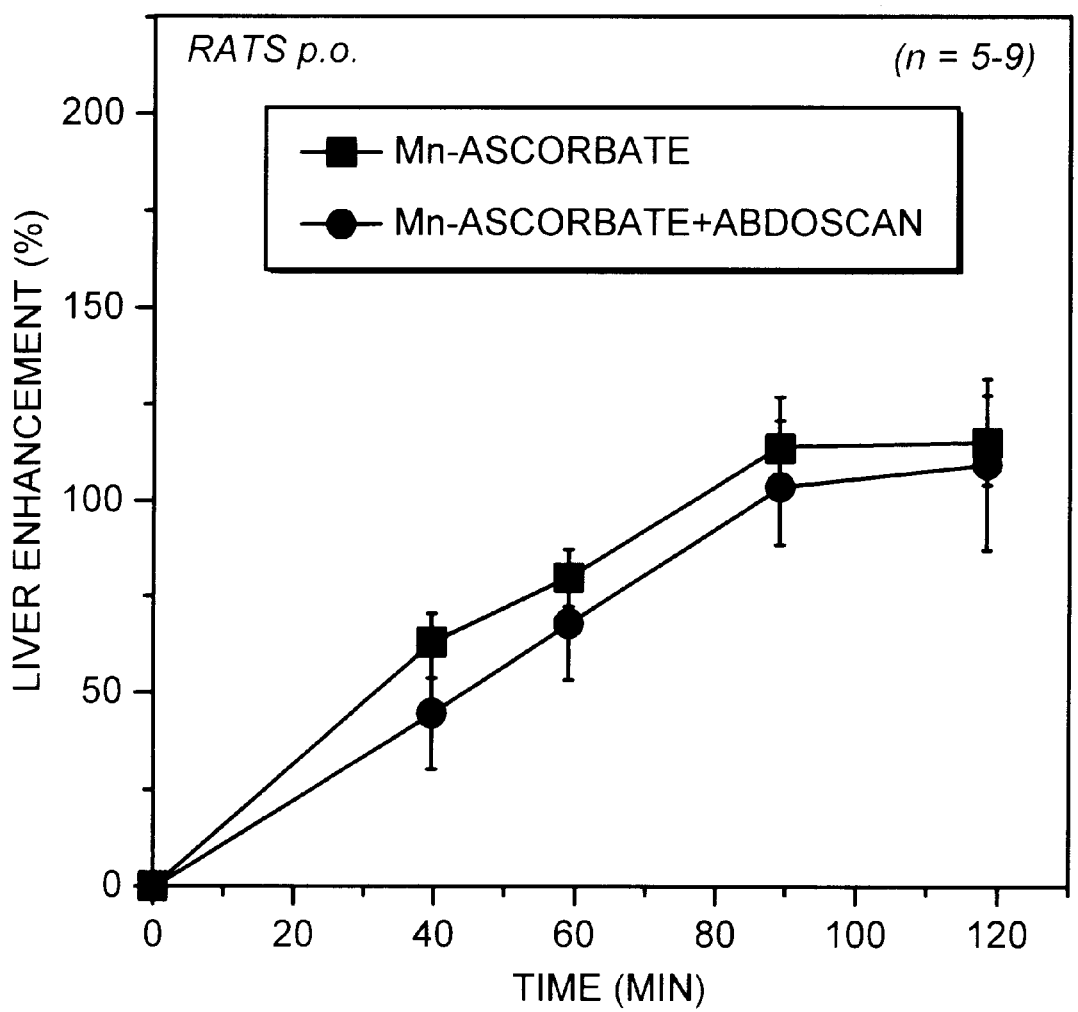
FIGS. 10 and 11 are graphs illustrating the effect of the addition of ABDOSCAN® to Mn-ascorbate on the enhancement of the liver.
Figure 11:
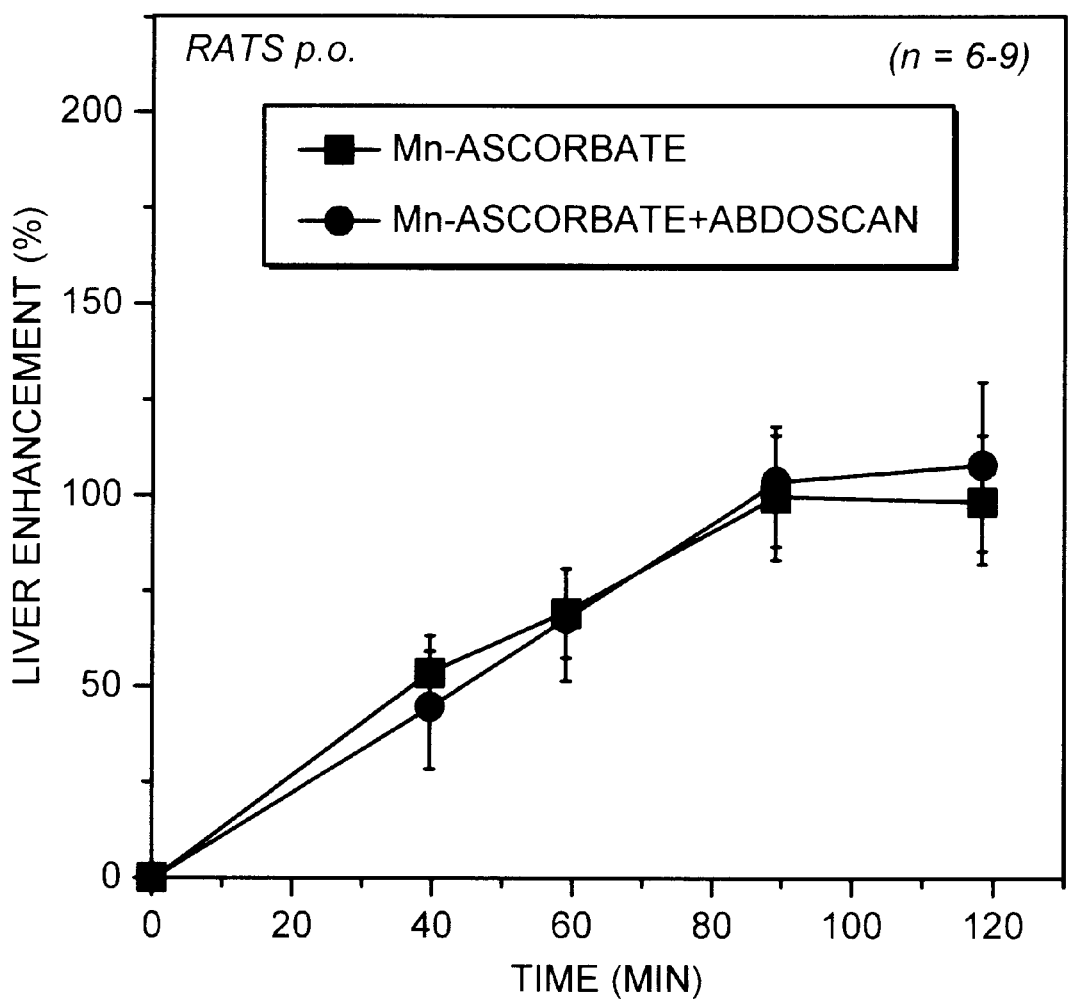
Figure 12:
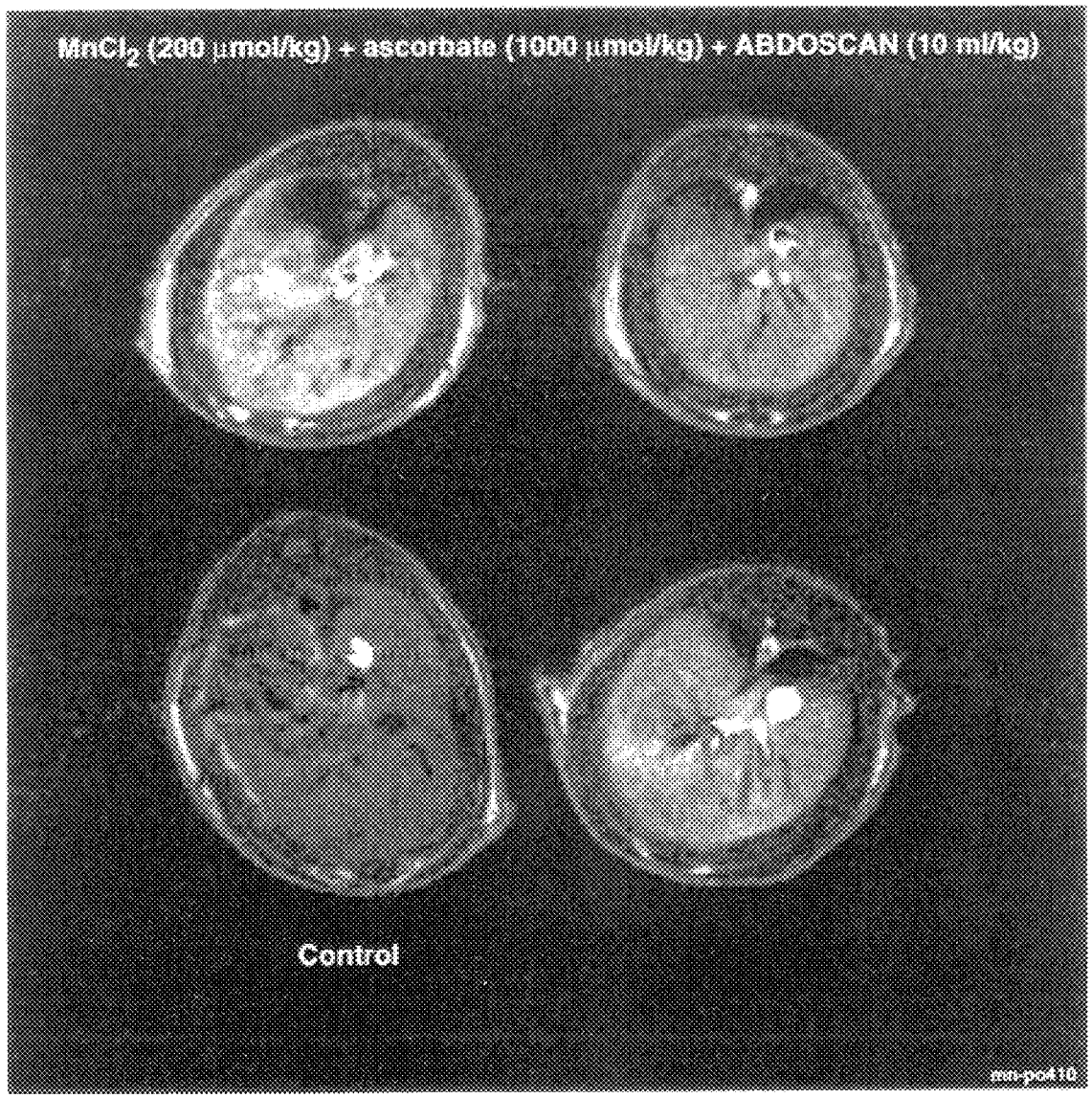
FIG. 12 illustrates transversal T1-weighted (SE 57/13; 2.4 T) liver images from a control rat and from three rats 2 hours after oral administration of 200 $\mu$mol/kg $MnCl_2$+1000 $\mu$mol/kg ascorbate+ABDOSCAN® (21 $\mu$mol/kg Fe). The addition of ABDOSCAN did not influence the signal intensity of the liver.
Figure 13:
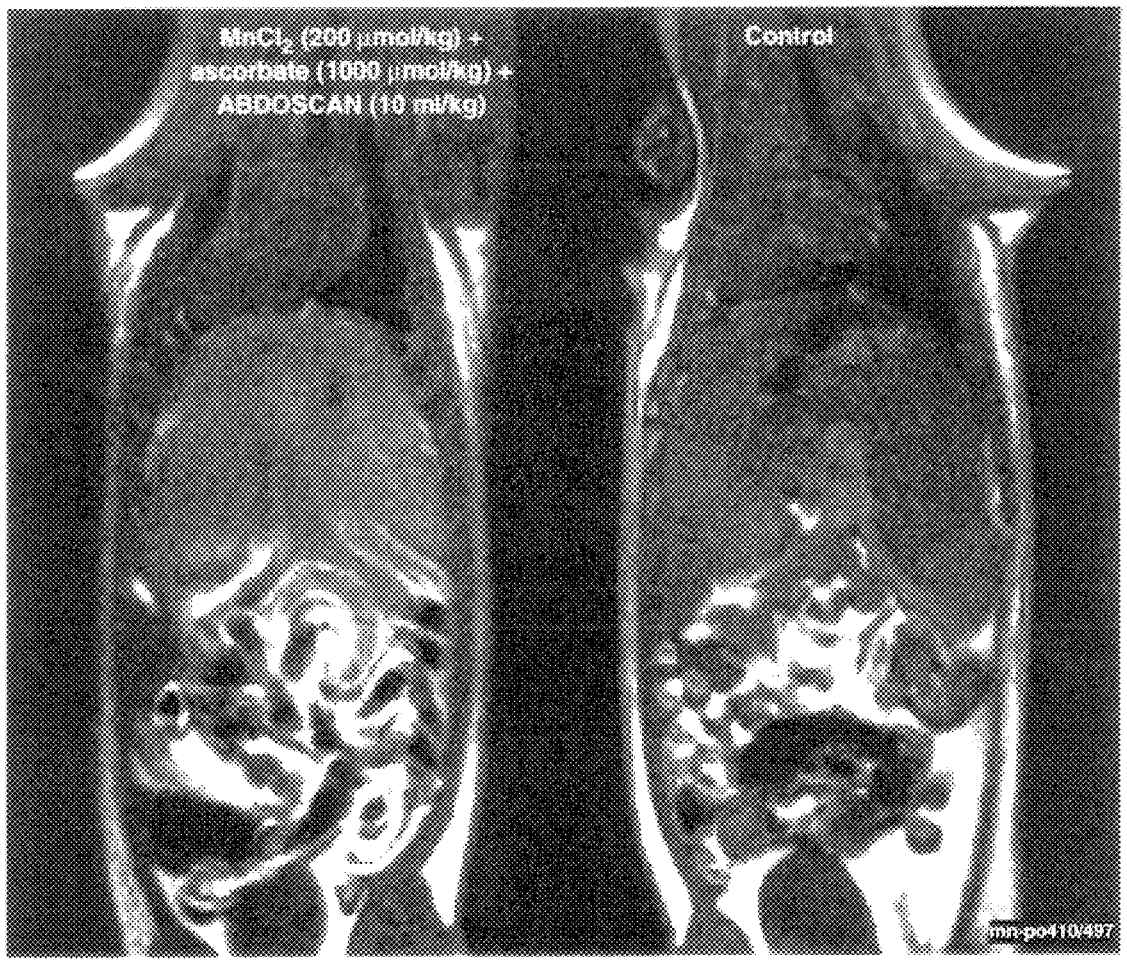
FIG. 13 illustrates coronal T1-weighted (SE 90/17; 2.4 T) liver images from a control rat and from a rat 2 hours after oral administration of 200 $\mu$mol/kg $MnCl_2$+1000 $\mu$mol/kg ascorbate+ABDOSCAN® (21 $\mu$mol/kg Fe). The signal intensity in the gastrointestinal lumen is markedly reduced after co-administration of $Mn^{2+}$ and ABDOSCAN.

For the measurement of the curves of FIGS. 10 and 11 the following materials were used:

| | | |
|---|---|---|
| $MnCl_2 \times 2H_2O$ | | 0.567 g |
| Ascorbic acid | | 3.08 g |
| ABDOSCAN ® | | 23.4 mg Fe |
| | | (one dose-package) |
| Water | ad | 200 ml |

EXAMPLE 1

| Oral Composition | | |
|---|---|---|
| MnCl$_2$ × 2H$_2$O | | 6.48 g |
| Ascorbic acid | | 35.2 g |
| Water | ad | 1000 ml |

The manganese chloride and ascorbic acid are dissolved in sterile deionised water. The dose for a 70 kg adult human would be 350 ml, taken orally.

EXAMPLE 2

| Oral Composition | | |
|---|---|---|
| MnCl$_2$ × 2H$_2$O | | 6.48 g |
| Kojic acid | | 11.4 g |
| Water | ad | 1000 ml |

The manganese chloride and kojic acid are dissolved in sterile deionised water. Tho dose for a 70 kg adult human would be 350 ml, taken orally.

EXAMPLE 3

| | Oral Compostion | | |
|---|---|---|---|
| A. | MnCl$_2$ × 2H$_2$O | | 13.0 g |
| | Water | ad | 1000 ml |
| B. | L-ascorbic acid 6-palmitate | | 66.4 g |
| | Polyethylene glycol 300 | ad | 1000 ml |

The dose for a 70 kg adult human would be 175 ml of A and 175 ml of B, taken orally.

EXAMPLE 4

| Oral Composition | | |
|---|---|---|
| MnCl$_2$ × 2H$_2$O | | 0.567 g |
| Ascorbic acid | | 3.08 g |
| ABDOSCAN ® | | 23.4 mg Fe |
| Water | ad | 200 ml |

The dose for a 70 kg adult human would be 4×200 ml, taken orally.

I claim:

1. A contrast medium composition comprising:
   (a) a first contrast agent comprising a physiologically tolerable manganese compound, and an uptake promoter capable of increasing uptake of manganese in a body, said uptake promoter comprising kojic acid or salt thereof, said first contrast agent having a manganese concentration of at least 0.3 mM or being in a dosage unit form containing at least 300 μmol manganese, together with
   (b) a second contrast agent which comprises a particulate ferromagnetic or superparamagnetic material.

2. A composition as claimed in claim 1 wherein the manganese compound is a chelate or a salt in which the manganese is present as Mn(II).

3. A composition as claimed in claim 1 comprising as both manganese compound and uptake promoter a manganese salt of kojic acid.

4. A composition as claimed in claim 1 wherein the first and second contrast agents have opposing contrast effects when used simultaneously in a single magnetic resonance imaging procedure.

5. A composition as claimed in claim 1 wherein the molar ratio of manganese to uptake promoter is from 1:1 to 1:6.

6. An MRI contrast agent kit comprising in a first container a first contrast agent comprising a physiologically tolerable manganese compound, kojic acid, or salt thereof, said first contrast agent having a manganese concentration of at least 0.3 mM or being in a dosage unit form containing at least 300 μmol manganese, and in a second container a second contrast agent as defined in claim 1.

7. An MRI contrast agent kit comprising:
   (a) in a first container a first contrast agent comprising a physiologically tolerable manganese compound, and an uptake promoter capable of increasing uptake of manganese in a body, said uptake promoter comprising kojic acid or salt thereof, and said first contrast agent having a manganese concentration of at least 0.3 mM or being in a dosage unit form containing at least 300 μmol manganese; and
   (b) in a second container a second contrast agent which comprises a particulate ferromagnetic or superparamagnetic material.

8. A kit as claimed in claim 7 wherein the molar ratio of manganese to uptake promoter is from 1:1 to 1:6.

9. A method of generating a magnetic resonance image of a human or non-human animal body, which method comprises administering into the gastrointestinal tract of a said body an effective amount of a composition as defined in claim 1 and generating a magnetic resonance image of the liver and abdomen of said body.

10. In a method of generating a magnetic resonance image of a human or non-human animal body, which method comprises administering into the gastrointestinal tract of a said body an effective amount of a composition comprising:
   (a) a first contrast agent comprising a physiologically tolerable manganese compound having a manganese concentration of at least 0.3mM or being in dosage unit form containing at least 300 μmol manganese, and the molar ratio of manganese to uptake promoter being from 1:1 to 1:6, together with
   (b) a second contrast agent which comprises a particulate ferromagnetic or superparamagnetic material,
   and generating an image of the liver and abdomen of said body, the improvement comprising the co-administration of an uptake promoter effective to increase absorption of manganese by the body, said uptake promoter comprising kojic acid or a salt thereof, wherein the first and second contrast agents have opposing contrast effects when used simultaneously in a single magnetic resonance imaging procedure.

* * * * *